(12) United States Patent
Lv et al.

(10) Patent No.: US 11,337,638 B2
(45) Date of Patent: May 24, 2022

(54) ECG SIGNAL PROCESSING METHOD AND APPARATUS

(71) Applicant: Huawei Technologies Co., Ltd., Shenzhen (CN)

(72) Inventors: Chao Lv, Beijing (CN); Yu Zhu, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 672 days.

(21) Appl. No.: 16/086,863

(22) PCT Filed: Dec. 30, 2016

(86) PCT No.: PCT/CN2016/113967
§ 371 (c)(1),
(2) Date: Sep. 20, 2018

(87) PCT Pub. No.: WO2018/082190
PCT Pub. Date: May 11, 2018

(65) Prior Publication Data
US 2019/0099103 A1 Apr. 4, 2019

(30) Foreign Application Priority Data
Nov. 3, 2016 (CN) .......................... 201610974448.2

(51) Int. Cl.
*A61B 5/366* (2021.01)
*A61B 5/00* (2006.01)
(Continued)

(52) U.S. Cl.
CPC .............. *A61B 5/366* (2021.01); *A61B 5/25* (2021.01); *A61B 5/316* (2021.01); *A61B 5/318* (2021.01);
(Continued)

(58) Field of Classification Search
CPC ................................ A61B 5/366; A61B 5/369
(Continued)

(56) References Cited

U.S. PATENT DOCUMENTS

| 4,958,641 A | 9/1990 | Digby et al. |
| 4,977,899 A | 12/1990 | Digby et al. |

(Continued)

FOREIGN PATENT DOCUMENTS

| CN | 1158077 A | 8/1997 |
| CN | 101467879 A | 7/2009 |

(Continued)

OTHER PUBLICATIONS

Machine Translation and Abstract of Chinese Publication No. CN103156599, Jun. 19, 2013, 12 pages.
(Continued)

*Primary Examiner* — Nadia A Mahmood
(74) *Attorney, Agent, or Firm* — Conley Rose, P.C.

(57) ABSTRACT

An electrocardiograph (ECG) signal processing method and apparatus to resolve a problem that relatively severe interference caused during single-arm measurement for single-lead ECG collection seriously affects accuracy of heart rate calculation and cardiac rhythm analysis. The method includes collecting, by a measurement device, an ECG signal, extracting a $k^{th}$ valid QRS complex of the ECG signal, calculating a $k^{th}$ time difference and a $(k+1)^{th}$ time difference, and determining whether the $k^{th}$ time difference and the $(k+1)^{th}$ time difference are target time differences. In this way, accuracy of ECG feature extraction is improved, the interference caused during the single-arm measurement is eliminated to the most extent, and the accuracy of heart rate calculation and cardiac rhythm analysis can be effectively guaranteed.

20 Claims, 6 Drawing Sheets

(51) Int. Cl.
*A61B 5/25* (2021.01)
*A61B 5/316* (2021.01)
*A61B 5/318* (2021.01)
*A61B 5/349* (2021.01)
*A61B 5/352* (2021.01)
*A61B 5/369* (2021.01)
*A61B 5/364* (2021.01)

(52) U.S. Cl.
CPC .............. *A61B 5/349* (2021.01); *A61B 5/352* (2021.01); *A61B 5/369* (2021.01); *A61B 5/7203* (2013.01); *A61B 5/364* (2021.01); *A61B 5/7221* (2013.01)

(58) Field of Classification Search
USPC ........................................................ 600/509
See application file for complete search history.

(56) References Cited

U.S. PATENT DOCUMENTS

| | | | |
|---|---|---|---|
| 5,758,654 A | 6/1998 | Burton-Krahn et al. |
| 6,126,595 A | 10/2000 | Amano et al. |
| 9,597,001 B2 | 3/2017 | Zigel et al. |
| 2014/0296714 A1 | 10/2014 | Kuroki et al. |

FOREIGN PATENT DOCUMENTS

| | | |
|---|---|---|
| CN | 103156599 A | 6/2013 |
| CN | 103892826 A | 7/2014 |
| CN | 104000581 A | 8/2014 |
| CN | 104586384 A | 5/2015 |
| CN | 105125199 A | 12/2015 |
| CN | 105286857 A | 2/2016 |
| CN | 105595979 A | 5/2016 |
| CN | 105997055 A | 10/2016 |
| JP | H05212006 A | 8/1993 |
| KR | 100198759 B1 | 6/1999 |

OTHER PUBLICATIONS

Machine Translation and Abstract of Chinese Publication No. CN104000581, Aug. 27, 2014, 20 pages.
Machine Translation and Abstract of Chinese Publication No. CN104586384, May 6, 2015, 13 pages.
Machine Translation and Abstract of Japanese Publication No. JPH05212006, Aug. 24, 1993, 13 pages.
Machine Translation and Abstract of Korean Publication No. KR100198759, Jun. 15, 1999, 20 pages.
Machine Translation and Abstract of Chinese Publication No. CN101467879, Jul. 1, 2009, 27 pages.
Foreign Communication From A Counterpart Application, Chinese Application No. 201680080606.8, Chinese Office Action dated Oct. 8, 2019, 6 pages.
Machine Translation and Abstract of Chinese Publication No. CN103892826, Jul. 2, 2014, 22 pages.
Machine Translation and Abstract of Chinese Publication No. CN105125199, Dec. 9, 2015, 20 pages.
Machine Translation and Abstract of Chinese Publication No. CN105286857, Feb. 3, 2016, 21 pages.
Machine Translation and Abstract of Chinese Publication No. CN105595979, May 25, 2016, 10 pages.
Machine Translation and Abstract of Chinese Publication No. CN105997055, Oct. 12, 2016, 17 pages.
Foreign Communication From A Counterpart Application, PCT Application No. PCT/CN2016/113967, English Translation of International Search Report dated Jul. 28, 2017, 2 pages.

ECG SIGNAL PROCESSING METHOD AND APPARATUS

CROSS-REFERENCE TO RELATED APPLICATIONS

This application is a U.S. National Stage of International Patent Application No. PCT/CN2016/113967 filed on Dec. 30, 2016, which claims priority to Chinese Patent Application No. 20161097444.2 filed on Nov. 3, 2016. Both of the aforementioned applications are hereby incorporated by reference in their entireties.

This application claims priority to CN Patent Application No. 201610974448.2, filed with the Chinese Patent Office on Nov. 3, 2016 and entitled "SINGLE-ARM ECG MEASUREMENT METHOD AND TERMINAL", which is incorporated herein by reference in its entirety.

TECHNICAL FIELD

The present invention relates to the terminal field, and in particular, to an ECG signal processing method and apparatus.

BACKGROUND

A conventional electrocardiograph (Electrocardiograph, ECG) measurement requires to be performed on a cross-cardiac area. An application scenario is limited, resulting in poor user experience.

In the prior art, a plurality of portable single-lead electrocardiograph collection and measurement solutions are proposed. Specifically, a single-lead electrocardiograph collection device usually uses a measurement mode such as a simulated limb lead I (for two hands) or a simulated chest lead (for a chest area and a cross-cardiac area). A signal obtained by using such measurement modes approximates an electrocardiograph signal obtained by a standard lead system. These measurement modes are currently widely used in portable electrocardiograph analysis service products. However, relatively severe interference may be introduced during single-arm measurement for single-lead electrocardiograph collection. For example, electromyography interference, motion artifacts, and the like are relatively obvious. This seriously affects accuracy of heart rate calculation and cardiac rhythm analysis.

SUMMARY

Embodiments of the present invention provide an ECG signal processing method and apparatus, to resolve a problem that relatively severe interference caused during single-arm measurement for single-lead electrocardiograph collection seriously affects accuracy of heart rate calculation and cardiac rhythm analysis.

According to a first aspect, an electrocardiograph ECG signal processing method includes:

collecting, by a measurement device, an ECG signal, and extracting a $k^{th}$ valid QRS complex of the ECG signal, where the QRS complex includes a first extreme point Q before a peak point R of an $i^{th}$ R wave, the peak point R of the $i^{th}$ R wave, and a second extreme point S after the peak point R of the $i^{th}$ R wave, where $i \geq 2$, $k \geq 2$, and $k \leq i$; further calculating a $k^{th}$ time difference and a $(k+1)^{th}$ time difference, where the $k^{th}$ time difference is a time difference between a peak point R of an R wave in the $k^{th}$ valid QRS complex and a peak point R of an R wave in a $(k+1)^{th}$ valid QRS complex, and the $(k+1)^{th}$ time difference is a time difference between the peak point R of the R wave in the $(k+1)^{th}$ valid QRS complex and a peak point R of an R wave in a $(k+2)^{th}$ valid QRS complex; and if the $k^{th}$ time difference and the $(k+1)^{th}$ time difference are within a preset range, and an absolute value of a difference between the $(k+1)^{th}$ time difference and the $k^{th}$ time difference is less than a preset threshold, determining, by the measurement device, the $k^{th}$ time difference and the $(k+1)^{th}$ time difference as target time differences; or if the $k^{th}$ time difference and the $(k+1)^{th}$ time difference are within a preset range, and an absolute value of a difference between the $(k+1)^{th}$ time difference and the $k^{th}$ time difference is greater than or equal to a preset threshold, determining, by the measurement device from the $k^{th}$ time difference and the $(k+1)^{th}$ time difference, a time difference that has a smaller deviation from an average time difference, as a target time difference, where the average time difference is an average value of all target time differences from a first time difference to a $(k-1)^{th}$ time difference, and the target time difference is used to calculate a heart rate value corresponding to the ECG signal.

Therefore, according to the ECG signal processing method provided in the embodiments of the present invention, valid QRS complexes are first extracted from the collected ECG signal, improving accuracy of electrocardiograph feature extraction. Then, time differences between peak points of R waves in adjacent valid QRS complexes are calculated. Further, a target time difference satisfying a requirement is selected based on the obtained time differences, so as to determine the heart rate value. In this way, the interference caused during the single-arm measurement is eliminated to the most extent, and the accuracy of heart rate calculation and cardiac rhythm analysis can be effectively guaranteed.

In a possible implementation, the extracting a $k^{th}$ valid QRS complex of the ECG signal includes: determining, by the measurement device, the first extreme point Q and the second extreme point S that correspond to the $i^{th}$ R wave; calculating a time difference between the first extreme point Q and the peak point R of the $i^{th}$ R wave, a time difference between the peak point R of the $i^{th}$ R wave and the second extreme point S, and a time difference between the first extreme point Q and the second extreme point S, where the time differences are recorded as a first time difference, a second time difference, and a third time difference respectively; and if the first time difference, the second time difference, and the third time difference are less than a corresponding first threshold, a corresponding second threshold, and a corresponding third threshold, respectively, the first extreme point corresponds to a Q wave, and the second extreme point corresponds to an S wave, determining, by the measurement device, that the $i^{th}$ R wave, the corresponding Q wave, and the corresponding S wave constitute the $k^{th}$ valid QRS complex.

Therefore, when the valid QRS complexes are extracted from the collected ECG signal by using the method provided in the embodiments of the present invention, the accuracy of ECG feature extraction is improved, and the accuracy of heart rate calculation and cardiac rhythm analysis are effectively guaranteed.

In a possible implementation, the method further includes:

calculating, by the measurement device, signal parameters corresponding to the ECG signal; calculating signal evaluation parameters based on at least one of the signal parameters; and determining a signal quality level of the ECG signal based on the signal evaluation parameters and preset evaluation thresholds corresponding to the signal evaluation parameters.

Therefore, according to the method provided in the embodiments of the present invention, the measurement device can evaluate different signal quality levels and notify a user by using a terminal. When signal quality is poor, the measurement device prompts the user to find out a cause such as a wrong wearing position or poor contact.

In a possible implementation, the signal parameters include a valid signal power, baseline drift, and in-band noise, and the signal evaluation parameters include a signal artifact ratio and a signal-to-noise-in-band ratio, where the signal artifact ratio is a function about the valid signal power and the baseline drift, and the signal-to-noise-in-band ratio is a function about the valid signal power and the in-band noise; and the determining, by the measurement device, a signal quality level of the ECG signal based on the signal evaluation parameters and preset evaluation thresholds corresponding to the signal evaluation parameters includes:

when determining that the signal artifact ratio is greater than a corresponding preset evaluation threshold, and that the signal-to-noise-in-band ratio is greater than a corresponding preset evaluation threshold, determining, by the measurement device, the signal quality level of the ECG signal as a first level;

when determining that the signal artifact ratio is less than or equal to a corresponding preset evaluation threshold, and that the signal-to-noise-in-band ratio is greater than a corresponding preset evaluation threshold, determining, by the measurement device, the signal quality level of the ECG signal as a second level;

when determining that the signal artifact ratio is greater than a corresponding preset evaluation threshold, and that the signal-to-noise-in-band ratio is less than or equal to a corresponding preset evaluation threshold, determining, by the measurement device, the signal quality level of the ECG signal as a third level; or when determining that the signal artifact ratio is less than or equal to a corresponding preset evaluation threshold, and that the signal-to-noise-in-band ratio is less than or equal to a corresponding preset evaluation threshold, determining, by the measurement device, the signal quality level of the ECG signal as a fourth level, where the first level is superior to the second level, the second level is superior to the third level, and the third level is superior to the fourth level.

Therefore, according to the method provided in the embodiments of the present invention, the obtained signal quality level can be used to predetermine quality of the collected signal, and the signal quality level is fed back to the user, so that the user can correct a wearing position when determining that the current signal quality level is poor. In this way, validity of the collected ECG signal is ensured, and signal measurement accuracy of a single-arm electrocardiograph measurement device is effectively guaranteed.

In a possible implementation, before the extracting a $k^{th}$ valid QRS complex of the ECG signal, the method further includes: performing, by the measurement device, filtering processing on the ECG signal, and obtaining a motion track of a user through fitting by using a tri-axis accelerometer; and comparing a filtered ECG signal with the motion track, and deleting, from the filtered ECG signal, an ECG waveform corresponding to duration in which a motion amplitude value is greater than a preset amplitude threshold in the motion track.

Therefore, according to the embodiments of the present invention, the measurement device compares the filtered ECG signal with the motion track, and deletes, from the filtered ECG signal, the ECG waveform corresponding to the duration in which the motion amplitude value is greater than the preset amplitude threshold in the motion track. In this way, effect of motion artifacts on ECG signal collection is eliminated, and validity of the collected ECG signal is improved.

According to a second aspect, a wearable device includes a processor, a memory, a heart rate collector, and a power supply, where the heart rate collector is configured to collect an ECG signal; the memory is configured to store an instruction; and the processor is configured to invoke the instruction in the memory to execute the first aspect or any one of the possible implementations of the first aspect.

Therefore, the wearable device proposed in the embodiments of the present invention first extracts valid QRS complexes from the collected ECG signal, improving accuracy of ECG feature extraction. Then, the wearable device calculates time differences between peak points of R waves in adjacent valid QRS complexes, and further selects, based on the obtained time differences, a target time difference satisfying a requirement, so as to determine a heart rate value. In this way, the interference caused during the single-arm measurement is eliminated to the most extent, and the accuracy of heart rate calculation and cardiac rhythm analysis can be effectively guaranteed.

In a possible implementation, the wearable device further includes an accelerometer sensor, where the acceleration sensor is configured to: detect acceleration in each direction, and obtain a motion track through fitting.

Therefore, the wearable device obtains the motion track through fitting by using the acceleration sensor, compares a filtered ECG signal with the motion track, and deletes, from the filtered ECG signal, an ECG waveform corresponding to duration in which a motion amplitude value is greater than a preset amplitude threshold in the motion track. In this way, effect of motion artifacts on ECG signal collection is eliminated, and validity of the collected ECG signal is improved.

According to a third aspect, this application provides an ECG signal processing apparatus, configured to perform the foregoing method according to any one of the first aspect or the possible implementations of the first aspect. Specifically, the apparatus includes units configured to perform the method according to any one of the first aspect or the possible implementations of the first aspect.

DESCRIPTION OF EMBODIMENTS

The following describes the embodiments of the present invention with reference to the accompanying drawings.

Figure 1:
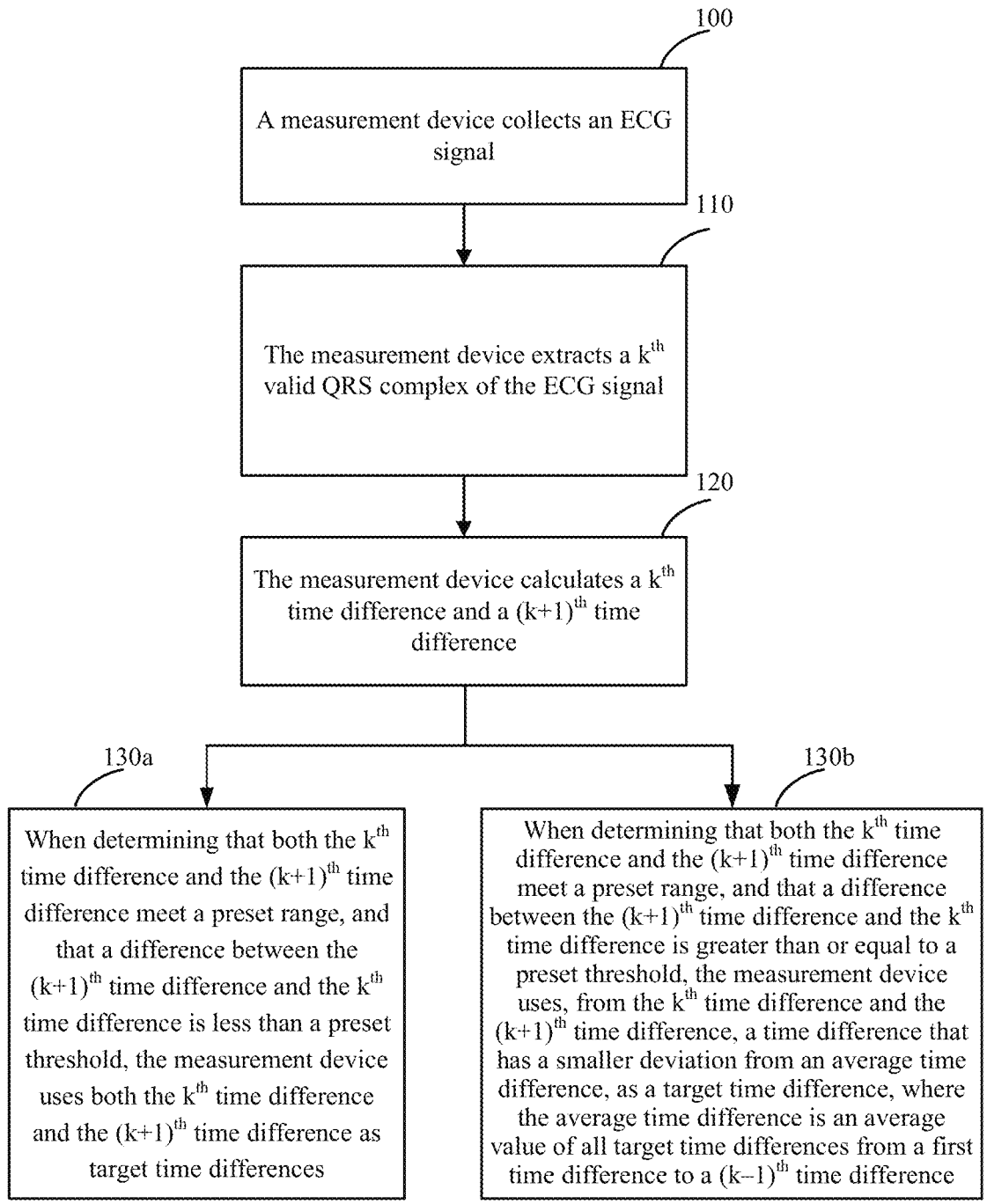
FIG. 1 is an overview flowchart of an ECG signal processing method according to an embodiment of the present invention.

Referring to FIG. 1, for a problem that relatively severe interference caused during single-arm measurement for single-lead electrocardiograph collection seriously affects accuracy of heart rate calculation and cardiac rhythm analysis, an embodiment of the present invention provides an ECG signal processing method. The method includes the following steps.

Step 100: A measurement device collects an ECG signal.

The measurement device mentioned in this embodiment of the present invention is a single-lead electrocardiograph collection device such as a wearable device.

That a measurement device collects an ECG signal may be: for example, a user wears the single-lead electrocardiograph collection device and switches the device on, and the device enters a self-test stage; if the device self-test succeeds, the device determines that the user wears the device correctly, and the device works properly; otherwise, the device prompts the user to correct a wearing position; and after the device enters a normal working state, the device starts to collect an ECG signal of the user.

Step 110: The measurement device extracts a $k^{th}$ valid QRS complex of the ECG signal, where the QRS complex includes a first extreme point Q before a peak point R of an $i^{th}$ R wave, the peak point R of the $i^{th}$ R wave, and a second extreme point S after the peak point R of the $i^{th}$ R wave, where i≥2, k≥2, and k≤i.

For each R wave in the ECG signal, the measurement device determines whether a peak point R of the current R wave and two extreme points on the left and right of the peak point R can constitute a valid QRS complex. Specifically, the measurement device may determine the valid QRS complex by using, but not limited to, the following method.

Figure 2:
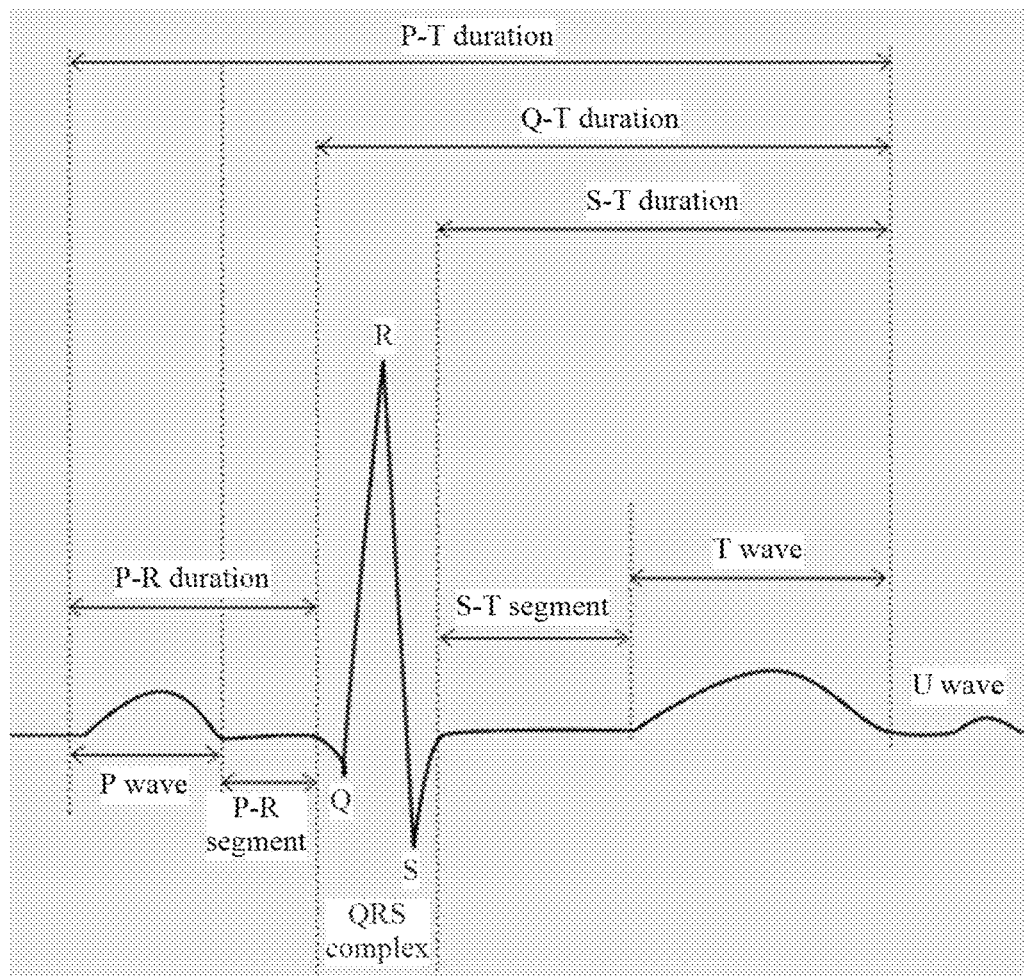
FIG. 2 is a schematic diagram of waveform features of a standard ECG signal according to an embodiment of the present invention.

FIG. 2 is a schematic diagram of waveform features of a standard ECG signal. As shown in FIG. 2, the measurement device may determine, based on the waveform features of the standard ECG signal, the first extreme point Q and the second extreme point S that correspond to the peak point R of the $i^{th}$ R wave. The first extreme point is the first extreme point Q before the peak point R of the $i^{th}$ R wave, and the second extreme point S is the first extreme point Q after the peak point R of the $i^{th}$ R wave, that is, two adjacent extreme points on the left and right sides of the peak point R of the R wave.

Further, the measurement device calculates a time difference between the first extreme point Q and the peak point R of the $i^{th}$ R wave, and records the time difference as a first time difference QS; calculates a time difference between the peak point R of the $i^{th}$ R wave and the second extreme point S, and records the time difference as a second time difference RS; and calculates a time difference between the first extreme point Q and the second extreme point S, and records the time difference as a third time difference QS.

When the measurement device determines that the first time difference, the second time difference, and the third time difference are less than a corresponding first threshold, a corresponding second threshold, and a corresponding third threshold, respectively, the measurement device determines that the first extreme point Q corresponds to a Q wave and the second extreme point S corresponds to an S wave, and further determines that the $i^{th}$ R wave, the corresponding Q wave, and the corresponding S wave constitute the $k^{th}$ valid QRS complex.

Specifically, the first threshold, the second threshold, and the third threshold herein may be set based on empirical values, provided that physiological features of a human body are met, and this embodiment of the present invention is not limited thereto. In this embodiment of the present invention, the first threshold ranges from 90 ms to 110 ms. For example, the first threshold may be 100 ms. The second threshold ranges from 90 ms to 110 ms. For example, the second threshold may be 100 ms. The third threshold ranges 140 ms to 160 ms. For example, the third threshold may be 150 ms. A determining condition for the valid QRS complex may be the QR<100 ms, the RS<100 ms, and the QS<150 ms.

When any one of the three time differences is greater than or equal to the corresponding threshold, the QRS complex is an invalid QRS complex. When the three time differences are all less than the corresponding thresholds, the QRS complex is a valid QRS complex.

It should be understood that because there may be an invalid QRS complex, k≤i.

Step 120: The measurement device calculates a $k^{th}$ time difference and a $(k+1)^{th}$ time difference.

The $k^{th}$ time difference is a time difference between a peak point R of an R wave in the $k^{th}$ valid QRS complex and a peak point R of an R wave in a $(k+1)^{th}$ valid QRS complex, and the $(k+1)^{th}$ time difference is a time difference between the peak point R of the R wave in the $(k+1)^{th}$ valid QRS complex and a peak point R of an R wave in a $(k+2)^{th}$ valid QRS complex.

Optionally, the $k^{th}$ valid QRS complex, the $(k+1)^{th}$ valid QRS complex, and the $(k+2)^{th}$ valid QRS complex are three consecutive complexes.

After determining all valid QRS complexes, the measurement device calculates a time difference between peak points R of two R waves in every two of all adjacent valid QRS complexes.

Step 130a: If the $k^{th}$ time difference and the $(k+1)^{th}$ time difference are within a preset range, and an absolute value of a difference between the $(k+1)^{th}$ time difference and the $k^{th}$ time difference is less than a preset threshold, the measurement device determines the $k^{th}$ time difference and the $(k+1)^{th}$ time difference as target time differences.

Step 130b: If the $k^{th}$ time difference and the $(k+1)^{th}$ time difference are within a preset range, and an absolute value of a difference between the $(k+1)^{th}$ time difference and the $k^{th}$ time difference is greater than or equal to a preset threshold, the measurement device determines, from the $k^{th}$ time difference and the $(k+1)^{th}$ time difference, a time difference that has a smaller deviation from an average time difference, as a target time difference, where the average time difference is an average value of all target time differences from a first time difference to a $(k-1)^{th}$ time difference.

The target time difference is used to calculate a heart rate value corresponding to the ECG signal.

In this embodiment of the present invention, when determining whether the $k^{th}$ time difference and the $(k+1)^{th}$ time difference are the target time differences, the measurement device first determines whether the $k^{th}$ time difference and the $(k+1)^{th}$ time difference are both within the preset range.

To be specific, the measurement device determines which of the time differences calculated in step 120 is within the preset range. The preset range herein is from 0.3 s to 1.5 s. The measurement device deletes the $k^{th}$ time difference or the $(k+1)^{th}$ time difference that does not meet the preset range. If both the $k^{th}$ time difference and the $(k+1)^{th}$ time difference are not within the preset range, the measurement device deletes both the $k^{th}$ time difference and the $(k+1)^{th}$ time difference. It should be understood that the deleted time difference is not the target time difference. A value of the foregoing preset range may be set and adjusted depending on an actual need. The foregoing values are merely examples and are not intended to limit this embodiment of the present invention.

When determining that the $k^{th}$ time difference and the $(k+1)^{th}$ time difference are within the preset range, the measurement device further determines whether the difference between the $k^{th}$ time difference and the $(k+1)^{th}$ time difference is less than the preset threshold value. The preset threshold herein may range from 0.1 s to 0.15 s. For example, the preset threshold may be 0.12 s. A value of the foregoing preset threshold may be set and adjusted depending on an actual need. The foregoing values are merely examples and are not intended to limit this embodiment of the present invention.

If the difference between the $(k+1)^{th}$ time difference and the $k^{th}$ time difference is less than the preset threshold, the measurement device determines the $k^{th}$ time difference and the $(k+1)^{th}$ time difference as the target time differences.

If the absolute value of the difference between the $(k+1)^{th}$ time difference and the $k^{th}$ time difference is greater than or equal to the preset threshold, the measurement device determines, from the $k^{th}$ time difference and the $(k+1)^{th}$ time difference, the time difference that has a smaller deviation from the average time difference, as the target time difference. The average time difference herein is the average value of all the target time differences from the first time difference to the $(k-1)^{th}$ time difference, that is, an average value of time differences that have not been deleted.

Further, the measurement device calculates a heart rate based on the obtained target time difference. Specifically, the measurement device measures target time differences within preset duration, calculates an average value of the target time differences based on the target time differences, and calculates the heart rate based on the average value of the target time differences. The heart rate value is equal to 60 divided by the average value of the target time differences.

In conclusion, according to the ECG signal processing method provided in this embodiment of the present invention, valid QRS complexes are first extracted from the collected ECG signal, improving accuracy of electrocardiograph feature extraction. Then, time differences between peak points of R waves in adjacent valid QRS complexes are calculated. Further, a target time difference satisfying a requirement is selected based on the obtained time differences, so as to determine the heart rate value. In this way, the interference caused during the single-arm measurement is eliminated to the most extent, and the accuracy of heart rate calculation and cardiac rhythm analysis can be effectively guaranteed.

Further, in this embodiment of the present invention, after step 100 is performed and before step 110 is performed, the measurement device may further perform the following operations.

The measurement device performs filtering processing on the ECG signal, and obtains a motion track of a user through fitting by using a tri-axis accelerometer.

Figure 3:
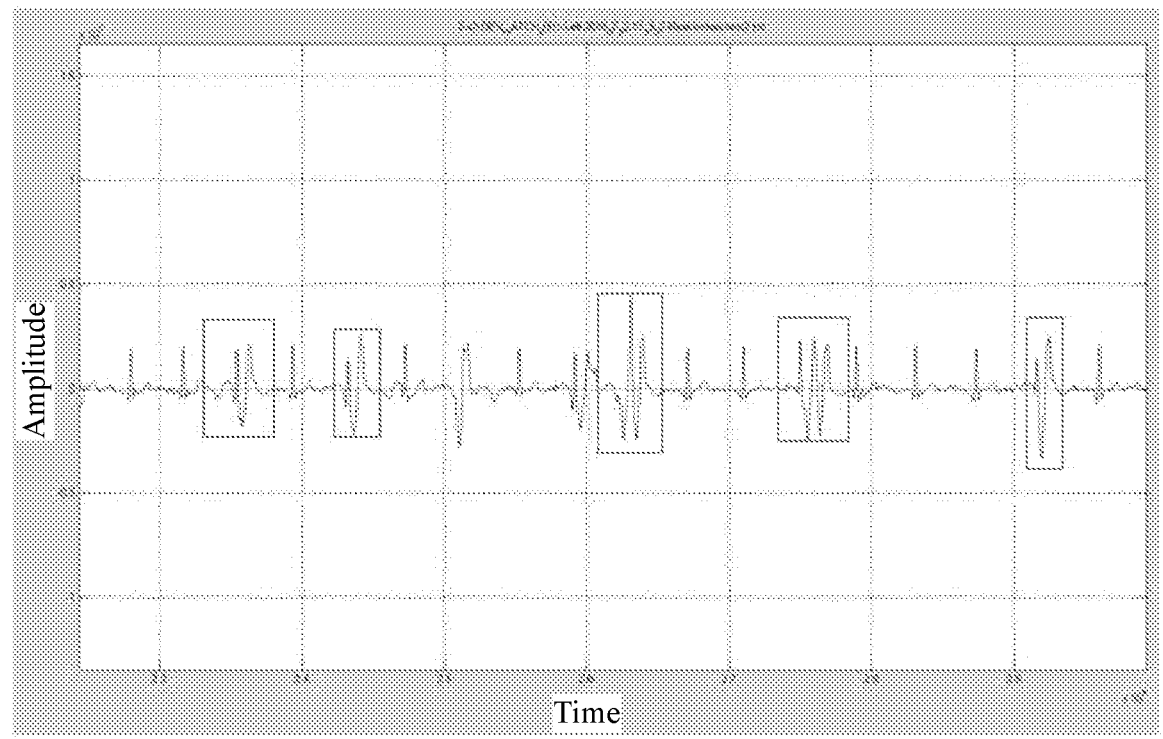
FIG. 3 is a waveform diagram of an ECG signal obtained after filtering processing according to an embodiment of the present invention.

For example, the measurement device performs filtering processing on the ECG signal by using a comb filter. Specifically, a center point of a stopband may be 1 Hz, 50 Hz, 100 Hz, 150 Hz, or the like, and a waveform obtained after filtering is shown in FIG. 3.

When obtaining the motion track through fitting by using the tri-axis accelerometer, the measurement device performs fitting based on three axes: an x axis, a y axis, and a z axis, to obtain a curve corresponding to the motion track.

According to this embodiment of the present invention, the measurement device compares a filtered ECG signal with the motion track, and deletes, from the filtered ECG signal, an ECG waveform corresponding to duration in which a motion amplitude value is greater than a preset amplitude threshold in the motion track. In this way, effect of motion artifacts on ECG signal collection is eliminated, and validity of the collected ECG signal is improved.

Further, after step 130a or step 130b, the measurement device may further continue to perform the following operations to determine signal quality of the ECG signal.

First, the measurement device calculates signal parameters corresponding to the ECG signal.

For example, the signal parameters herein may be, but are not limited to, the following parameters: a valid signal power (denoted as PW_ECG), power frequency interference (denoted as PW_50), baseline drift (denoted as PW_1), and in-band noise (denoted as PW_NB).

An original signal power is denoted as ECG_original. PW_50 and PW_1 may be obtained by performing frequency-domain transform on an original signal, and PW_ECG may be obtained by calculating an amplitude value of the R wave, a width of the QRS, an amplitude value of a T wave, and a width of the T wave.

$$PW\_NB = ECG\_{original} - PW\_50 - PW\_1 - PW\_ECG$$

The foregoing signal parameters can be calculated by using a method provided in the prior art.

Then, the measurement device calculates signal evaluation parameters based on at least one of the signal parameters.

The signal evaluation parameters herein may be a signal artifact ratio (Signal Artifact Ratio, SAR) and a signal-to-noise-in-band ratio (Signal Noise in Band Ratio, SNBR).

$$SAR = lg(PW\_ECG/PW\_1), \text{ and } SNBR = lg(PW\_ECG/PW\_NB).$$

Finally, the measurement device determines a signal quality level of the ECG signal based on the signal evaluation parameters and preset evaluation thresholds corresponding to the signal evaluation parameters.

Further, the measurement device may notify the user of the signal quality level of the ECG signal by a voice prompt, a pop-up dialog box, or other means. This is not limited herein.

Specifically, when the signal evaluation parameters are the SAR and the SNBR, and if the SAR is greater than a corresponding preset evaluation threshold (denoted as TH_SAR) and the SNBR is greater than a corresponding preset evaluation threshold (denoted as TH_SNBR), the measurement device determines the signal quality level of the ECG signal as a first level.

If the SAR is less than or equal to the TH_SAR, and the SNBR is greater than the TH_SNBR, the measurement device determines the signal quality level of the ECG signal as a second level.

If the SAR is greater than the TH_SAR, and the SNBR is less than or equal to the TH_SNBR, the measurement device determines the signal quality level of the ECG signal as a third level.

If the SAR is less than or equal to the TH_SAR, and the SNBR is less than or equal to the TH_SNBR, the measurement device determines the signal quality level of the ECG signal as a fourth level.

The first level is superior to the second level, the second level is superior to the third level, and the third level is superior to the fourth level.

Table 1 is a correspondence table of signal quality levels. Specifically, as shown in Table 1, the signal quality levels are classified based on a threshold combination of the SAR and the SNBR. There are four signal quality levels (SQL): 1 to 4, where 1 represents excellent, the others are ranked in decreasing order, and 4 represents that a feature cannot be extracted due to large noise. Different signal quality levels can be notified to the user by using a terminal. When the signal quality is poor, the user is prompted to find out a cause such as a wrong wearing position or poor contact.

TABLE 1

| Signal level | Signal quality evaluation |
| --- | --- |
| 1 | SAR > TH_SAR && SNBR > TH_SNBR |
| 2 | SAR < TH_SAR && SNBR > TH_SNBR |
| 3 | SAR > TH_SAR && SNBR < TH_SNBR |
| 4 | SAR < TH_SAR && SNBR < TH_SNBR |

The ECG signal processing method provided in this embodiment of the present invention is described below by using a specific electrocardiogram measurement process as an example.

Step (Step) 1: A user wears a single-lead electrocardiogram collection device and switches the device on, and the device enters a self-test stage to predetermine quality of a collected signal.

Specifically, after performing step 1 to step 4 once completely, the device determines whether a quantity of target time differences continuously measured within 1 minute meets a preset condition. If the quantity of the target time differences measured within 1 minute meets the preset condition, the device determines that the user wears the device correctly and the device works properly; otherwise, the device prompts the user to correct a wearing position.

Figure 4A:
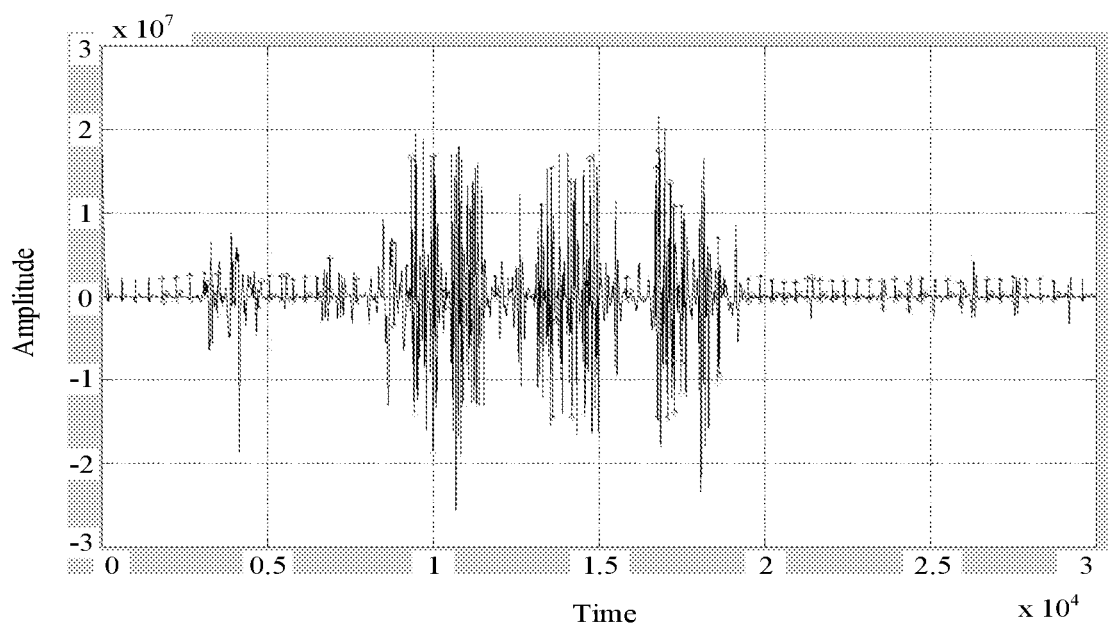
FIG. 4(a) is a schematic diagram of electrode position shift when a user incorrectly wears a device according to an embodiment of the present invention.
Figure 4B:
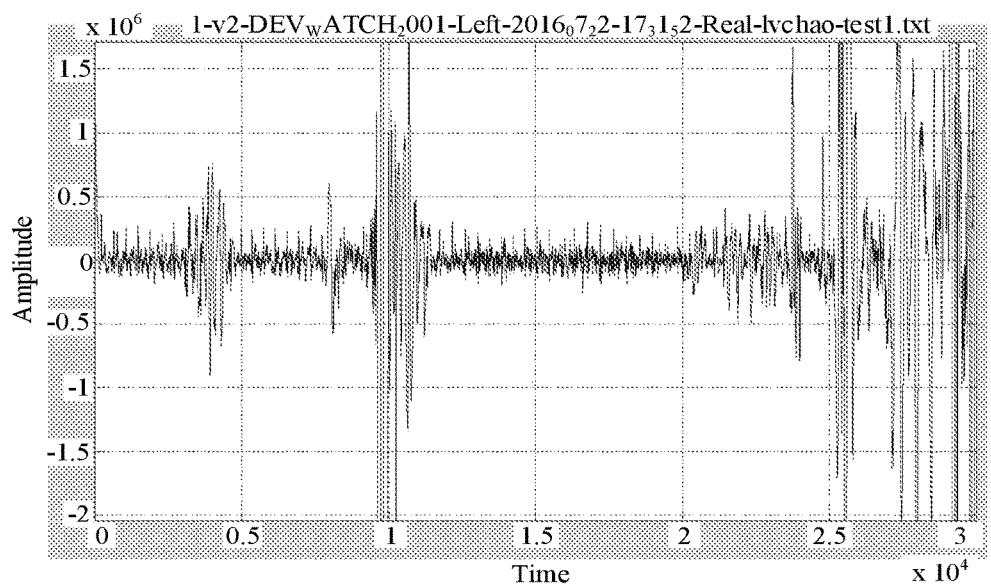
FIG. 4(b) is a schematic diagram of a normal electrode position when a user correctly wears a device according to an embodiment of the present invention.

For example, when the user incorrectly wears the device, an electrode position shifts, and the waveform in this case is shown in FIG. 4(a). When the user correctly wears the device, the electrode position is normal, and the waveform in this case is shown in FIG. 4(b).

Step 2: After the device works properly, the device performs filtering and artifact processing on an obtained ECG signal.

Specifically, the device filters the collected ECG signal by using a comb filter, obtains a motion track through fitting based on a tri-axis accelerometer (fitting based on the x axis, the y axis, and the z axis), determines, in the filtered ECG signal, an ECG waveform corresponding to duration in which an amplitude value is greater than a preset amplitude threshold in a corresponding curve of a motion track, and deletes the corresponding ECG waveform, so as to enhance accuracy of the ECG signal.

Step 3: Extract a valid ECG feature, mainly including a valid QRS complex and a target time difference.

Specifically, a QRS joint detection method is used. An R wave is first detected, a point Q and a point S are then determined successively based on extreme points before and after the R wave, and a QR interval, an RS interval, and a QS interval are compared with corresponding thresholds. For example, when the QR<100 ms, the RS<100 ms, and the QS<150 ms, the QRS complex is determined as a valid QRS complex; otherwise, the QRS complex is determined as an invalid QRS complex. Values of the QR, RS, and QS may be set and adjusted based on an actual need. The foregoing values are merely examples and are not intended to limit this embodiment of the present invention.

Figure 5:
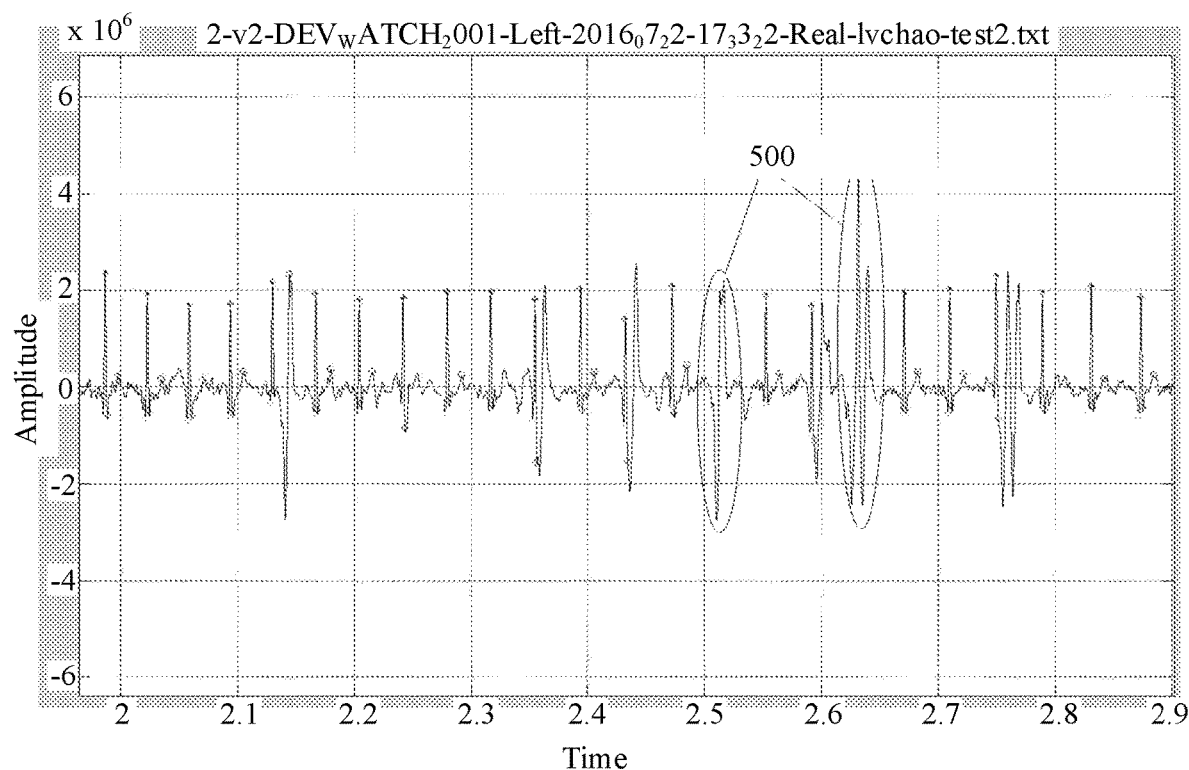
FIG. 5 is a schematic diagram of an invalid QRS complex according to an embodiment of the present invention.

As shown in FIG. 5, waveforms marked by an ellipse 500 exceed a reasonable width of a QRS complex and are also local peak points, but the waveforms do not meet the condition: the QR<100 ms, the RS<100 ms, and the QS<150 ms. Therefore, the waveforms marked by the ellipse are invalid QRS complexes and are not to be incorrectly determined as valid QRS complexes.

Further, a time difference between peak points R of two R waves in every two consecutive valid QRS complexes, that is, an RR interval, is calculated. If the RR interval falls within 0.3 s to 1.5 s, the condition is met, and whether a next condition is met continues to be determined; otherwise, the RR interval is excluded. Further, after the foregoing condition is met, whether a difference between adjacent RR intervals is less than 0.12 s is determined. If the difference between the adjacent RR intervals is less than 0.12 s, the two RR intervals are reserved. In other words, the two RR intervals are both the target time differences. If the difference between the adjacent RR intervals is not less than 0.12 s, one RR interval that has a larger deviation from an average RR interval is excluded, and the other RR interval is reserved as the target time difference. Specially, the average RR interval is an average value of previously reserved target time differences. The values of the RR interval and the difference between the adjacent RR intervals may be set and adjusted depending on an actual need. The foregoing values are merely examples and are not intended to limit this embodiment of the present invention.

Further, an average RR value of all selected target time differences is obtained. For example, 30 target time differences are obtained in one minute based on the foregoing measurement process, an average value of the 30 target time differences is calculated, and then a heart rate is calculated based on the average value of the 30 target time differences. The heart rate is equal to 60 divided by the average value of the 30 target time differences.

Therefore, the waveform that may affect a measurement result is removed by using the foregoing method, so as to improve the accuracy of electrocardiograph feature extraction, and effectively guarantee signal measurement validity of a single-arm electrocardiograph measurement device.

Step 4: Evaluate the signal quality of the ECG signal in real time.

First, signal parameters are calculated, including a valid signal power (PW_ECG), power frequency interference (PW_50), baseline drift (PW_1), in-band noise (PW_NB), and the like. Further, signal evaluation parameters, SAR=lg (PW_ECG/PW_1) and SNBR=lg(PW_ECG/PW_NB), are obtained. Assuming that TH_SAR=0 dB and TH_SNBR=10 dB, a signal quality level of the current ECG signal is further determined based on Table 1, to prompt the user of validity of the collected ECG signal. Values of the TH_SAR and the TH_SNBR may be set and adjusted depending on an actual need. The foregoing values are merely examples and are not intended to limit this embodiment of the present invention.

For example, in step 1, the signal quality level of the current ECG signal may be determined based on a result obtained in step 4, and if a current signal quality level is 4, the user may be prompted to find out a cause and measure again.

The signal quality level obtained in step 4 may be used as a criterion to predetermine quality of the collected signal in step 1 and the signal quality level is fed back to the user, so that the user can correct a wearing position when determining that the current signal quality level is relatively poor. In this way, validity of the collected ECG signal is ensured, and signal measurement accuracy of the single-arm electrocardiograph measurement device is effectively guaranteed.

An embodiment of the present invention provides a wearable device, including a processor, a memory, a heart rate collector, and a power supply. For example, the wearable device herein may be a sport arm band, a heart rate monitor, or a heart rate patch. When the wearable device is a heart rate patch, the heart rate patch may communicate with another terminal (for example, a mobile phone) by using a Bluetooth module.

Figure 6:
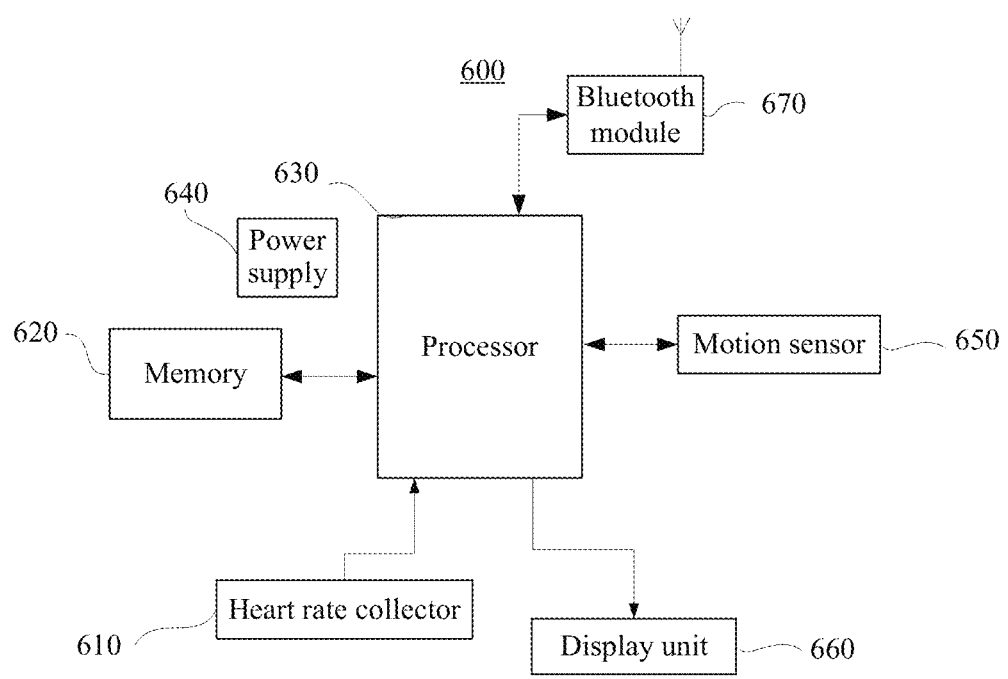
FIG. 6 is a schematic structural diagram of a wearable device according to an embodiment of the present invention.

The following describes components of the wearable device 600 in detail with reference to FIG. 6.

The heart rate collector 610 is configured to collect an ECG signal.

The memory 620 is configured to store an instruction.

The processor 630 is configured to invoke the instruction in the memory to execute the foregoing ECG signal processing process.

The power supply 640 is configured to supply power to the wearable device.

In a possible design, the wearable device further includes a motion sensor 650.

The motion sensor 650 is configured to: detect acceleration in each direction, and obtain a motion track through fitting.

In a possible design, the wearable device further includes a display unit 660, a Bluetooth module 670, and the like.

The wearable device provided in this embodiment of the present invention is configured to execute the method embodiment corresponding to FIG. 1. Therefore, for implementations of the wearable device provided in this embodiment of the present invention, refer to the implementations of the method, and details are not repeated herein.

In conclusion, according to the method provided in this embodiment of the present invention, and with reference to laws of physiological changes in motion, the accuracy of electrocardiograph feature extraction is improved, and the signal measurement accuracy of a single-arm electrocardiograph measurement device is effectively guaranteed.

Based on a same inventive concept, an embodiment of the present invention further provides an ECG signal processing apparatus, and the apparatus is configured to execute the method embodiment corresponding to FIG. 1. Therefore, for implementations of the ECG signal processing apparatus provided in this embodiment of the present invention, refer to the implementations of the method, and details are not repeated herein.

Figure 7:
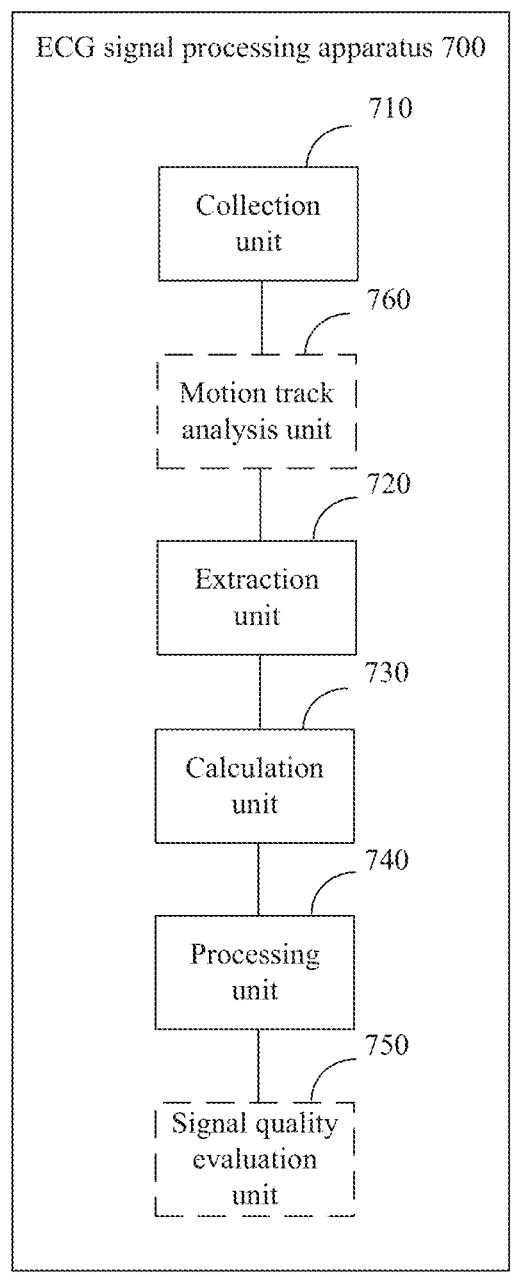
FIG. 7 is a schematic structural diagram of an ECG signal processing apparatus according to an embodiment of the present invention.

Referring to FIG. 7, an embodiment of the present invention provides an ECG signal processing apparatus, including: a collection unit 710, an extraction unit 720, a calculation unit 730, and a processing unit 740.

The collection unit 710 is configured to collect an ECG signal.

The extraction unit 720 is configured to extract a $k^{th}$ valid QRS complex of the ECG signal, where the QRS complex includes a first extreme point Q before a peak point R of an $i^{th}$ R wave, the peak point R of the $i^{th}$ R wave, and a second extreme point S after the peak point R of the $i^{th}$ R wave, where $i \geq 2$, $k \geq 2$, and $k \leq i$.

The calculation unit 730 is configured to calculate a $k^{th}$ time difference and a $(k+1)^{th}$ time difference, where the $k^{th}$ time difference is a time difference between a peak point R of an R wave in the $k^{th}$ valid QRS complex and a peak point R of an R wave in a $(k+1)^{th}$ valid QRS complex, and the $(k+1)^{th}$ time difference is a time difference between the peak point R of the R wave in the $(k+1)^{th}$ valid QRS complex and a peak point R of an R wave in a $(k+2)^{th}$ valid QRS complex.

The processing unit 740 is configured to: if the $k^{th}$ time difference and the $(k+1)^{th}$ time difference are within a preset range, and an absolute value of a difference between the $(k+1)^{th}$ time difference and the $k^{th}$ time difference is less than a preset threshold, determine the $k^{th}$ time difference and the $(k+1)^{th}$ time difference as target time differences; or if the $k^{th}$ time difference and the $(k+1)^{th}$ time difference are within a preset range, and an absolute value of a difference between the $(k+1)^{th}$ time difference and the $k^{th}$ time difference is greater than or equal to a preset threshold, determine, from the $k^{th}$ time difference and the $(k+1)^{th}$ time difference, a time difference that has a smaller deviation from an average time difference, as a target time difference, where the average time difference is an average value of all target time differences from a first time difference to a $(k-1)^{th}$ time difference.

The target time difference is used to calculate a heart rate value corresponding to the ECG signal.

In a possible implementation, the extraction unit 720 is configured to: when extracting $k^{th}$ valid QRS complex of the ECG signal, determine the first extreme point Q and the second extreme point S that correspond to the $i^{th}$ R wave; and calculate a time difference between the first extreme point Q and the peak point R of the $i^{th}$ R wave, a time difference between the peak point R of the $i^{th}$ R wave and the second extreme point S, and a time difference between the first extreme point Q and the second extreme point S, where the time differences are recorded as a first time difference, a second time difference, and a third time difference respectively; and if the first time difference, the second time difference, and the third time difference are less than a corresponding first threshold, a corresponding second threshold, and a corresponding third threshold, respectively, the first extreme point Q corresponds to a Q wave, the second extreme point S corresponds to an S wave, and the $i^{th}$ R wave, the corresponding Q wave, and the corresponding S wave constitute the $k^{th}$ valid QRS complex.

In a possible implementation, the apparatus further includes:

a signal quality evaluation unit 750, configured to calculate signal parameters corresponding to the ECG signal;

calculate signal evaluation parameters based on at least one of the signal parameters; and determine a signal quality level of the ECG signal based on the signal evaluation parameters and preset evaluation thresholds corresponding to the signal evaluation parameters.

In a possible implementation, the signal parameters include a valid signal power, baseline drift, and in-band noise.

The signal evaluation parameters include a signal artifact ratio and a signal-to-noise-in-band ratio. The signal artifact ratio is a function about the valid signal power and the baseline drift, and the signal-to-noise-in-band ratio is a function about the valid signal power and the function of the in-band noise.

the signal quality evaluation unit 750 is configured to: when determining the signal quality level of the ECG signal based on the signal evaluation parameters and the preset evaluation thresholds corresponding to the signal evaluation parameters, when determining that the signal artifact ratio is greater than a corresponding preset evaluation threshold, and that the signal-to-noise-in-band ratio is greater than a corresponding preset evaluation threshold, determine the signal quality level of the ECG signal as a first level;

when determining that the signal artifact ratio is less than or equal to a corresponding preset evaluation threshold, and that the signal-to-noise-in-band ratio is greater than a corresponding preset evaluation threshold, determine the signal quality level of the ECG signal as a second level;

when determining that the signal artifact ratio is greater than a corresponding preset evaluation threshold, and that the signal-to-noise-in-band ratio is less than or equal to a corresponding preset evaluation threshold, determine the signal quality level of the ECG signal as a third level; or when determining that the signal artifact ratio is less than or equal to a corresponding preset evaluation threshold, and that the signal-to-noise-in-band ratio is less than or equal to a corresponding preset evaluation threshold, determine the signal quality level of the ECG signal as a fourth level, where the first level is superior to the second level, the second level is superior to the third level, and the third level is superior to the fourth level.

In a possible implementation, the apparatus further includes a motion track analysis unit 760, configured to: before the $k^{th}$ valid QRS complex of the ECG signal is extracted, perform filtering processing on the ECG signal, and obtain a motion track of a user through fitting by using a tri-axis accelerometer; and compare a filtered ECG signal with the motion track, and delete, from the filtered ECG signal, an ECG waveform corresponding to duration in which a motion amplitude value is greater than a preset amplitude threshold in the motion track.

A person of ordinary skill in the art may understand that all or a part of the steps in each of the foregoing method of the embodiments may be implemented by a program instructing a processor. The foregoing program may be stored in a computer readable storage medium. The storage medium may be a non-transitory (English: non-transitory) medium such as a random-access memory, read-only memory, a flash memory, a hard disk, a solid state drive, a magnetic tape (English: magnetic tape), a floppy disk (English: floppy disk), an optical disc (English: optical disc), or any combination thereof.

The present invention is described with reference to the flowcharts and/or block diagrams of the method and the device according to the embodiments of the present invention. It should be understood that computer program instructions may be used to implement each process or each block in the flowcharts and the block diagrams and a combination of a process and a block in the flowcharts and the block diagrams. These computer program instructions may be provided for a general-purpose computer, a dedicated computer, an embedded processor, or a processor of any other programmable data processing device to generate a machine, so that the instructions executed by a computer or a processor of any other programmable data processing device generate an apparatus for implementing a specific function in one or more processes in the flowcharts and in one or more blocks in the block diagrams.

The foregoing descriptions are merely examples of embodiments of the present invention, but are not intended to limit the protection scope of the present invention. Any variation or replacement readily figured out by a person skilled in the art within the technical scope disclosed in the present invention shall fall within the protection scope of the present invention. Therefore, the protection scope of the present invention shall be subject to the protection scope of the claims.

What is claimed is:

1. An electrocardiograph (ECG) signal processing method performed by a measurement device, the method comprising:

collecting, by a heart rate collector of the measurement device, an ECG signal;

extracting a $k^{th}$ valid QRS complex from the ECG signal, the QRS complex comprising a first extreme point (Q) before a peak point (R) of an $i^{th}$ R wave, the R of the $i^{th}$ R wave, and a second extreme point (S) after the R of the $i^{th}$ R wave, i≥two, k≥two, and the k≤the i;

calculating a $k^{th}$ time difference and a $(k+1)^{th}$ time difference, the $k^{th}$ time difference being a time difference between an R of an R wave in the $k^{th}$ valid QRS complex and an R of an R wave in a $(k+1)^{th}$ valid QRS complex, and the $(k+1)^{th}$ time difference being a time difference between the R of the R wave in the $(k+1)^{th}$ valid QRS complex and an R of an R wave in a $(k+2)^{th}$ valid QRS complex;

setting, in the measurement device, the $k^{th}$ time difference and the $(k+1)^{th}$ time difference as target time differences when the $k^{th}$ time difference and the $(k+1)^{th}$ time difference are within a preset range, and an absolute value of a difference between the $(k+1)^{th}$ time difference and the $k^{th}$ time difference is less than a preset threshold;

setting, in the measurement device and based on the $k^{th}$ time difference and the $(k+1)^{th}$ time difference, a time difference having a smaller deviation from an average time difference as a target time difference when the $k^{th}$ time difference and the $(k+1)^{th}$ time difference are within the preset range, and the absolute value of the difference between the $(k+1)^{th}$ time difference and the $k^{th}$ time difference is greater than or equal to the preset threshold, the average time difference being an average value of all target time differences from a first time difference to a $(k-1)^{th}$ time difference; and calculating a heart rate value corresponding to the ECG signal using the target time difference.

2. The ECG signal processing method of claim 1, wherein extracting the $k^{th}$ valid QRS complex from the ECG signal comprises:

determining the Q and the S corresponding to the $i^{th}$ R wave;

calculating a first time difference between the Q and the R of the $i^{th}$ R wave, a second time difference between the R of the $i^{th}$ R wave and the S, and a third time difference between the Q and the S; and determining that the $i^{th}$ R wave, a corresponding Q wave, and a corresponding S wave constitute the $k^{th}$ valid QRS complex in response to the Q corresponding to the corresponding Q wave, and the S corresponding to the corresponding S wave when the first time difference between the Q and the R of the $i^{th}$ R wave is less than a corresponding first threshold, the second time difference is less than a corresponding second threshold, and the third time difference is less than a corresponding third threshold.

3. The ECG signal processing method of claim 1, further comprising:
calculating signal parameters corresponding to the ECG signal;
calculating signal evaluation parameters based on at least one of the signal parameters; and
determining a signal quality level of the ECG signal based on the signal evaluation parameters and preset evaluation thresholds corresponding to the signal evaluation parameters.

4. The ECG signal processing method of claim 3, wherein the signal parameters comprise a valid signal power, a baseline drift, and an in-band noise, wherein the signal evaluation parameters comprise a signal artifact ratio and a signal-to-noise-in-band ratio, wherein the signal artifact ratio is a function of the valid signal power and the baseline drift, wherein the signal-to-noise-in-band ratio is a function of the valid signal power and the in-band noise, and wherein determining the signal quality level of the ECG signal comprises determining the signal quality level of the ECG signal as a first level when the signal artifact ratio is greater than a corresponding first preset evaluation threshold and the signal-to-noise-in-band ratio is greater than a corresponding second preset evaluation threshold.

5. The ECG signal processing method of claim 4, wherein determining the signal quality level of the ECG signal comprises determining the signal quality level of the ECG signal as a second level when the signal artifact ratio is less than or equal to the corresponding first preset evaluation threshold and the signal-to-noise-in-band ratio is greater than the corresponding second preset evaluation threshold.

6. The ECG signal processing method of claim 5, wherein determining the signal quality level of the ECG signal comprises determining the signal quality level of the ECG signal as a third level when the signal artifact ratio is greater than the corresponding first preset evaluation threshold and the signal-to-noise-in-band ratio is less than or equal to the corresponding second preset evaluation threshold.

7. The ECG signal processing method of claim 6, wherein determining the signal quality level of the ECG signal comprises determining the signal quality level of the ECG signal as a fourth level when the signal artifact ratio is less than or equal to the corresponding first preset evaluation threshold and the signal-to-noise-in-band ratio is less than or equal to the corresponding second preset evaluation threshold, and wherein the first level is superior to the second level, the second level is superior to the third level, and the third level is superior to the fourth level.

8. The ECG signal processing method of claim 1, wherein before extracting the $k^{th}$ valid QRS complex from the ECG signal, the method further comprises:
performing filtering processing on the ECG signal;
obtaining a motion track of a user through fitting using a tri-axis accelerometer;
comparing a filtered ECG signal with the motion track; and
deleting, from the filtered ECG signal, an ECG waveform corresponding to a duration in which a motion amplitude value is greater than a preset amplitude threshold in the motion track.

9. A measurement device, comprising:
a heart rate collector;
a memory configured to store instructions; and
a processor coupled to the heart rate collector and the memory and configured to execute the instructions to cause the measurement device to be configured to:
collect, using the heart rate collector, an electrocardiograph (ECG) signal;
extract a $k^{th}$ valid QRS complex from the ECG signal, the QRS complex comprising a first extreme point (Q) before a peak point (R) of an $i^{th}$ R wave, the R of the $i^{th}$ R wave, and a second extreme point (S) after the R of the $i^{th}$ R wave, i≥two, k≥two, and the k≤the i;
calculate a $k^{th}$ time difference and a $(k+1)^{th}$ time difference, the $k^{th}$ time difference being a time difference between an R of an R wave in the $k^{th}$ valid QRS complex and an R of an R wave in a $(k+1)^{th}$ valid QRS complex, and the $(k+1)^{th}$ time difference being a time difference between the R of the R wave in the $(k+1)^{th}$ valid QRS complex and an R of an R wave in a $(k+2)^{th}$ valid QRS complex;
set, in the measurement device, the $k^{th}$ time difference and the $(k+1)^{th}$ time difference as target time differences when the $k^{th}$ time difference and the $(k+1)^{th}$ time difference are within a preset range, and an absolute value of a difference between the $(k+1)^{th}$ time difference and the $k^{th}$ time difference is less than a preset threshold;
set, in the measurement device and based on the $k^{th}$ time difference and the $(k+1)^{th}$ time difference, a time difference having a smaller deviation from an average time difference, as a target time difference when the $k^{th}$ time difference and the $(k+1)^{th}$ time difference are within the preset range, and the absolute value of the difference between the $(k+1)^{th}$ time difference and the $k^{th}$ time difference is greater than or equal to the preset threshold, wherein the average time difference is an average value of all target time differences from a first time difference to a $(k-1)^{th}$ time difference; and
calculate a heart rate value corresponding to the ECG signal using the target time difference.

10. The measurement device of claim 9, wherein the instructions further cause the measurement device to be configured to:
determine the Q and the S corresponding to the $i^{th}$ R wave;
calculate a first time difference between the Q and the R of the $i^{th}$ R wave, a second time difference between the R of the $i^{th}$ R wave and the S, and a third time difference between the Q and the S; and
determine that the $i^{th}$ R wave, a corresponding Q wave, and a corresponding S wave constitute the $k^{th}$ valid QRS complex in response to the Q corresponding to the corresponding Q wave, and the S corresponding to the corresponding S wave when the first time difference between the Q and the R of the $i^{th}$ R wave is less than a corresponding first threshold, the second time difference is less than a corresponding second threshold, and the third time difference is less than a corresponding third threshold.

11. The measurement device of claim 9, wherein the instructions further cause the measurement device to be configured to:
calculate signal parameters corresponding to the ECG signal;
calculate signal evaluation parameters based on at least one of the signal parameters; and determine a signal quality level of the ECG signal based on the signal evaluation parameters and preset evaluation thresholds corresponding to the signal evaluation parameters.

12. The measurement device of claim 11, wherein the signal parameters comprise a valid signal power, a baseline drift, and an in-band noise, wherein the signal evaluation parameters comprise a signal artifact ratio and a signal-to-noise-in-band ratio, wherein the signal artifact ratio is a function of the valid signal power and the baseline drift, wherein the signal-to-noise-in-band ratio is a function of the valid signal power and the in-band noise, and wherein the instructions further cause the measurement device to be configured to determine the signal quality level of the ECG signal as a first level when the signal artifact ratio is greater than a corresponding first preset evaluation threshold and the signal-to-noise-in-band ratio is greater than a corresponding second preset evaluation threshold.

13. The measurement device of claim 12, wherein the instructions further cause the measurement device to be configured to determine the signal quality level of the ECG signal as a second level when the signal artifact ratio is less than or equal to the corresponding first preset evaluation threshold and the signal-to-noise-in-band ratio is greater than the corresponding second preset evaluation threshold.

14. The measurement device of claim 13, wherein the instructions further cause the measurement device to be configured to determine the signal quality level of the ECG signal as a third level when the signal artifact ratio is greater than the corresponding first preset evaluation threshold and the signal-to-noise-in-band ratio is less than or equal to the corresponding second preset evaluation threshold.

15. The measurement device of claim 14, wherein the instructions further cause the measurement device to be configured to determine the signal quality level of the ECG signal as a fourth level when the signal artifact ratio is less than or equal to the corresponding first preset evaluation threshold and the signal-to-noise-in-band ratio is less than or equal to the corresponding second preset evaluation threshold, and wherein the first level is superior to the second level, the second level is superior to the third level, and the third level is superior to the fourth level.

16. The measurement device of claim 9, further comprising a tri-axis accelerometer coupled to the processor, wherein before extracting the $k^{th}$ valid QRS complex of the ECG signal, the instructions further cause the measurement device to:
perform filtering processing on the ECG signal;
obtain a motion track of a user through fitting using the tri-axis accelerometer;
compare a filtered ECG signal with the motion track; and
delete, from the filtered ECG signal, an ECG waveform corresponding to a duration in which a motion amplitude value is greater than a preset amplitude threshold in the motion track.

17. The measurement device of claim 9, wherein the measurement device is a wearable device.

18. The measurement device of claim 10, wherein the corresponding first threshold is within a range of 90 milliseconds to 110 milliseconds.

19. The measurement device of claim 10, wherein the corresponding second threshold is within a range of 90 milliseconds to 110 milliseconds.

20. The measurement device of claim 10, wherein the corresponding third threshold is within a range of 140 milliseconds to 160 milliseconds.

* * * * *